United States Patent
Kawashima

(10) Patent No.: US 8,309,360 B2
(45) Date of Patent: Nov. 13, 2012

(54) REAGENT FOR ANALYZING URINE AND METHOD FOR ANALYZING URINE

(75) Inventor: Yasuyuki Kawashima, Kobe (JP)

(73) Assignee: Sysmex Corporation, Hyogo (JP)

( * ) Notice: Subject to any disclaimer, the term of this patent is extended or adjusted under 35 U.S.C. 154(b) by 1577 days.

(21) Appl. No.: 11/723,626

(22) Filed: Mar. 21, 2007

(65) Prior Publication Data
US 2007/0254331 A1 Nov. 1, 2007

(30) Foreign Application Priority Data
Mar. 22, 2006 (JP) ................. 2006-078007

(51) Int. Cl.
*G01N 33/48* (2006.01)
*G01N 21/75* (2006.01)
*G01N 21/76* (2006.01)

(52) U.S. Cl. ............... 436/63; 436/10; 436/17; 436/164; 436/172; 436/174; 422/73; 422/82.05; 422/82.08; 422/82.09; 435/29; 435/34

(58) Field of Classification Search ............... None
See application file for complete search history.

(56) References Cited

U.S. PATENT DOCUMENTS

| | | | |
|---|---|---|---|
| 5,891,733 A | 4/1999 | Inoue | |
| 7,632,683 B2 * | 12/2009 | Kawashima et al. | ........... 436/63 |
| 2004/0185447 A1 | 9/2004 | Maples et al. | |
| 2006/0073601 A1 * | 4/2006 | Kawashima et al. | ........... 436/63 |

FOREIGN PATENT DOCUMENTS

| | | |
|---|---|---|
| EP | 1 405 918 A1 | 4/2004 |
| WO | WO 2006/007479 A2 | 1/2006 |

OTHER PUBLICATIONS

Fernández-Collazo et al., "Elimination of Spermatozoa in the Urine of Isolated Male Rats," J. Reprod. Fert., (1971) 27, pp. 14-147.*

* cited by examiner

*Primary Examiner* — Sreeni Padmanabhan
*Assistant Examiner* — Jody Karol
(74) *Attorney, Agent, or Firm* — Sughrue Mion, PLLC

(57) ABSTRACT

A reagent for analyzing urine is described. The reagent comprises a fungus membrane damaging agent for damaging a cellular membrane of yeast-like fungus in urine; a first dye for staining yeast-like fungus so that a fluorescent intensity of damaged yeast-like fungus becomes more intense than that of erythrocyte in urine; and a second dye for staining sperm in urine so that a fluorescent intensity of sperm becomes more intense than that of the damaged yeast-like fungus.

6 Claims, 5 Drawing Sheets

FLH=110

FLH=87

FLH=87

FLH=165

REAGENT FOR ANALYZING URINE AND METHOD FOR ANALYZING URINE

BACKGROUND OF THE INVENTION

1. Field of the Invention

The present invention relates to a reagent for analyzing a urine particle contained in urine and a method for analyzing the urine particle.

2. Description of the Related Art

In diseases such as infectious diseases inflammatory lesion, degenerative lesion, lithiasis and tumor of a renal/urinal tract system, various urine particles appear in urine depending on each disease. Examples of the urine particle include erythrocyte, yeast-like fungus, and sperm. Analysis of these components in urine is important for early detection of a disease of a renal/urinal tract system and presuming an abnormal site.

Examples of a reagent for analyzing a urine particle in urine include reagents disclosed in U.S. Pat. No. 5,891,733. U.S. Pat. No. 5,891,733 discloses a reagent for analyzing solid components in urine comprising a first dye which is a fused benzene derivative such as 3'-dimethyl-2,2'-oxacarbocyanine iodide (DiOCl3)), and a second fluorescent dye which can stain damaged leukocytes such as ethidium bromide and propridium iodide. And, it is described that the first dye can bind to a cellular membrane, and since dyeability of erythrocyte for the first dye and dyeability of yeast-like fungus for the first dye are different, a difference in dyeability between erythrocyte and yeast-like fungus is grasped as a difference in a fluorescent intensity and, based on this, it becomes possible to differentiate erythrocyte and yeast-like fungus. However, U.S. Pat. No. 5,891,733 does not describe differentiation of sperm from other components in urine when urine containing sperm is used as a specimen.

SUMMARY OF THE INVENTION

The scope of the present invention is defined solely by the appended claims, and is not affected to any degree by the statements within this summary.

An object of the present invention is to provide a reagent and a method which can accurately differentiate sperm among urine particles contained in urine.

A first aspect of the present invention relates to a reagent for analyzing urine, comprising:

a fungus membrane damaging agent for damaging a cellular membrane of yeast-like fungus in urine;

a first dye for staining yeast-like fungus so that a fluorescent intensity of damaged yeast-like fungus becomes more intense than that of erythrocyte in urine; and a second dye for staining sperm in urine so that a fluorescent intensity of sperm becomes more intense than that of the damaged yeast-like fungus.

A second aspect of the present invention relates to a reagent kit for analyzing urine, comprising:

a first reagent comprising a fungus membrane damaging agent for damaging a cellular membrane of yeast-like fungus in urine;

a second reagent comprising a first dye and a second dye, wherein the first dye stains yeast-like fungus so that a fluorescent intensity of damaged yeast-like fungus becomes more intense than that of erythrocyte in urine, and the second dye stains sperm in urine so that a fluorescent intensity of sperm becomes more intense than that of the damaged yeast-like fungus.

A third aspect of the present invention relates to a method for analyzing urine, comprising the steps of:

preparing a measuring sample by fluorescent staining treatment for urine, wherein the fluorescent staining treatment damages a cellular membrane of yeast-like fungus in urine without substantially damaging a cellular membrane of erythrocyte in urine, and stains erythrocyte, yeast-like fungus and sperm in urine so that a fluorescent intensity of yeast-like fungus becomes more intense than that of erythrocyte, and a fluorescent intensity of sperm becomes more intense than that of yeast-like fungus;

obtaining scattered light information and fluorescence information from the measuring sample by irradiating the measuring sample with light; and differentiating sperm contained in the measuring sample based on the scattered light information and the fluorescence information.

DESCRIPTION OF THE PREFERRED EMBODIMENTS

Reagent for Analyzing Urine

Figure 1:
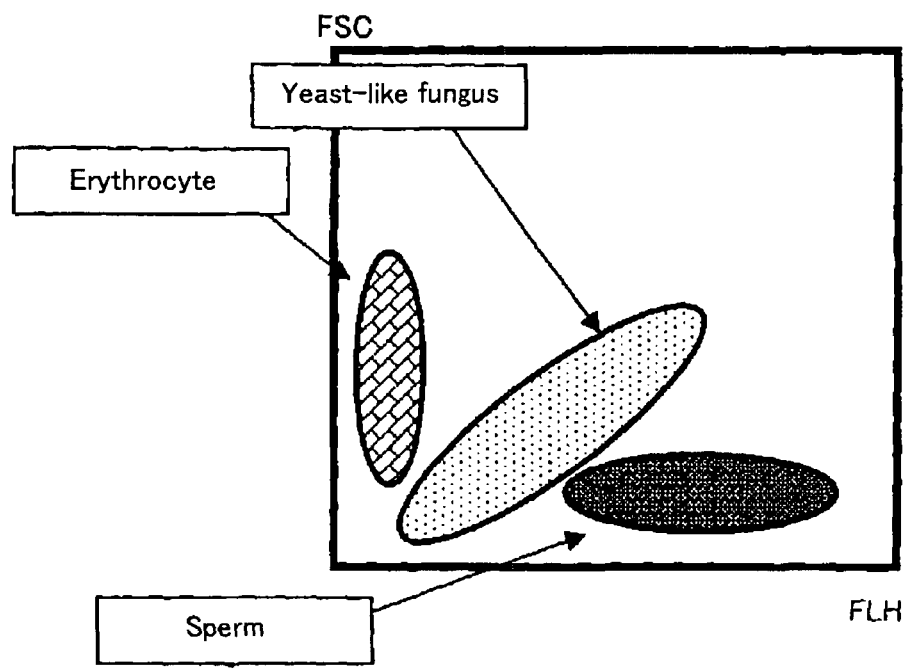
FIG. 1 is a conceptional view of a scattering diagram obtained when urine containing sperm and yeast-like fungus is measured using a reagent for analyzing urine containing a first dye and a second dye.

A reagent for analyzing urine of the present embodiment comprises:

a substance which does not substantially damage a cellular membrane of erythrocyte in urine, and damages a cellular membrane of yeast-like fungus in urine (hereinafter, the substance is referred to as "fungus membrane damaging agent");

a first dye which is capable of staining yeast-like fungus so that a fluorescent intensity of a damaged yeast-like fungus becomes more intense than a fluorescent intensity of not substantially damaged erythrocyte; and a second dye which stains sperm so that a fluorescent intensity of sperm becomes more intense than the fluorescent intensity of damaged yeast-like fungus. When the reagent for analyzing urine is used, sperm among urine particles contained in urine can be accurately differentiated.

As used herein, the "damage of cellular membrane" refers to perforation of a pore in a cellular membrane through which a specific agent can pass.

(1) Fungus Membrane Damaging Agent

The fungus membrane damaging agent is an agent which damages a cellular membrane of yeast-like fungus in urine. The agent has an action of perforating a pore in a part of a cellular membrane of yeast-like fungus. If a pore is generated in a cellular membrane of a cell with the agent, when the cell is treated with a dye, the pore allows the dye to enter the cell. In a cell which underwent damage in a cellular membrane, not only a surface of the cellular membrane but also a substance (e.g. nucleic acid etc.) in the cell is stained with a dye and, as a result, dyeability with the dye becomes higher than that of a cell which did not undergo damage in a membrane. Therefore, by using the fungus membrane damaging agent and a dye which can stain a urine particle having a damaged cellular membrane, it becomes possible to differentiate a urine particle having the damaged cellular membrane and a urine particle having a not damaged cellular membrane.

It is preferable that the fungus membrane damaging agent does not hemolyze erythrocyte. It is further preferable that the agent does not substantially damage a cellular membrane of sperm.

Examples of such the fungus membrane damaging agent include a nonionic organic compound having a benzene ring described in United States Application Publication Number 2006-0073601. Specific examples include aromatic alcohols such as benzyl alcohol, phenethyl alcohol, phenol, 1-phenoxy-2-propanol, 2-phenoxyethanol and the like, phenyl acetate, and benzothiazole compounds such as 2-aminobenzothiazole and benzothiazole. Among them, 2-phenoxyethanol is preferably used.

The fungus membrane damaging agent may be contained in a reagent at such a concentration that, upon mixing of urine and the reagent, a cellular membrane of erythrocyte in urine is not substantially damaged, and a cellular membrane of yeast-like fungus can be damaged. A concentration of the fungus membrane damaging agent may be appropriately selected depending on the damaging ability thereof. Letting a concentration in a measuring sample prepared by mixing urine and a reagent to be a final concentration, for example, when the fungus membrane damaging agent is 2-phenoxyethanol, the final concentration is preferably 0.3 to 1.5%, more preferably 0.5 to 1.0%, further preferably 0.5 to 0.7%.

(2) First Dye

The first dye is a dye which can stain yeast-like fungus so that a fluorescent intensity of damaged yeast-like fungus becomes more intense than a fluorescent intensity of not substantially damaged erythrocyte. The first dye can fluorescently stain a damaged cell by penetrating into a cytoplasm thorough a pore of a cellular membrane generated by damaging. Usually, an amount of penetration of a dye into a cytoplasm is associated with an extent of damage of a cellular membrane.

Fungus has various sizes due to variety of its kind. In a large fungus, its size is similar to that of erythrocyte in some cases and, in that case, it is difficult to distinguish the large fungus and erythrocyte by the scattered light. For this reason, it is desired that they can be distinguished by a difference in dyeability with a dye. Since the first dye can penetrate into a cytoplasm through a pore of a cellular membrane generated with the fungus membrane damaging agent and stain yeast-like fungus, a difference in dyeability between a fungus which underwent damage in a membrane and erythrocyte which did not undergo damage in a membrane can be produced by using the first dye. That is, the first dye penetrates more into a cytoplasm of yeast-like fungus which underwent damage with the fungus membrane damaging agent than erythrocyte and sperm which did not substantially undergo damage. Therefore, dyeability of yeast-like fungus with first dye becomes higher than dyeability of erythrocyte and sperm with first dye. In addition, since the first dye is a dye which can fluorescently stain, dyeability with the dye can be expressed as fluorescent intensity.

The first dye is not particularly limited as far as it can fluorescently stain a substance in a cell. This is because dyeability with the first dye depends mainly on an extent of damage of a cellular membrane generated with the fungus membrane damaging agent as described above. In addition, as the first dye, a dye which fluorescently stains a nucleic acid is preferably used since this is effective in distinguishing dyeability between erythrocyte having no nucleus and yeast-like fungus having a nucleus.

In addition, it is preferable that the first dye stains a cellular membrane of erythrocyte or sperm which did not undergo damage in a cellular membrane, and it is preferable that the first dye stains a cellular membrane of a sperm more intense than a cellular membrane of erythrocyte. Since a cellular membrane of erythrocyte or sperm is not substantially damaged with an action of the fungus membrane damaging agent, the first dye can not substantially pass through a cellular membrane. However, by using the aforementioned first dye, erythrocyte and sperm are stained and, further, a cellular membrane of sperm is stained more intense than a cellular membrane of erythrocyte. Thereby, differentiation between erythrocyte and sperm becomes easy.

It is preferable that such the first dye is selected from the group consisting of fluorescent dyes represented by the formula (1), the formula (2) and the formula (3) of the following chemical formulas.

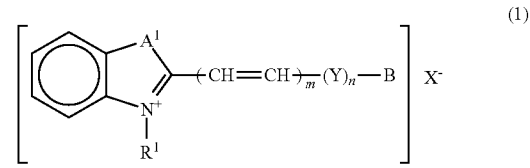

(1)

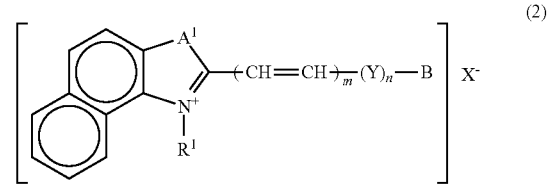

(2)

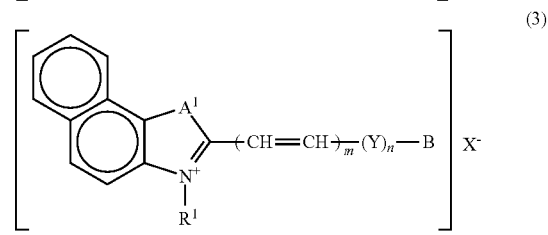

(3)

In the formula (1), the formula (2) and formula (3), A1 is an oxygen atom, a sulfur atom, a selenium atom, or a $C(CH_3)_2$. R1 is a lower alkyl group. X is a halogen or perchloric acid. Y is a —CH= or —NH—. And, m is 1 or 2, and n is 0 or 1. B is a phenyl group substituted with two lower alkoxy groups or one di-lower alkylamino group, or a residue represented by the following formula (4) or the following formula (5). A lower alkyl group of the di-lower alkylamino group may be substituted with a cyano group.

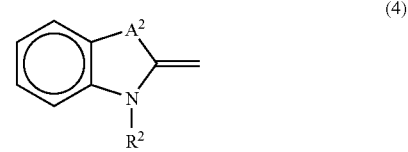

(4)

In the formula (4), A2 is an oxygen atom, a sulfur atom, or a C(CH$_3$)$_2$ group. R2 is a lower alkyl group.

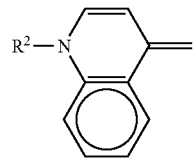
(5)

In the formula (5), R2 is a lower alkyl group.

In the formulas (1) to (5), A1 and A2 may be the same or different. And, R1 and R2 may be the same or different.

A fluorescent dye having the aforementioned chemical structure can bind to a cellular membrane. Further, the fluorescent dye having the aforementioned chemical structure is bound to or absorbed onto a cellular membrane of sperm or erythrocyte which did not undergo damage in a cellular membrane and, at the same time, penetrates into a cytoplasm through a pore of a cellular membrane of yeast-like fungus which underwent damage in a cellular membrane, and stains a nucleic acids.

The lower alkyl group means an alkyl group of a carbon number of 1 to 6, and examples include methyl, ethyl, propyl, butyl, isobutyl, pentyl, hexyl and the like. Examples of the halogen atom of X include fluorine, chlorine, bromine and iodine. The phenyl group substituted with two lower alkoxy groups in B refers to a phenyl group substituted with two C1-3 alkoxy groups, preferably C1-2 alkoxy groups (e.g. methoxy group, ethoxy group). Specific examples include a 2,6-dimethoxyphenyl group, and a 2,6-diethoxyphenyl group. And, the phenyl group substituted with a di-lower alkylamino group in B refers to a phenyl group substituted with a C1-3 alkylamino group, preferably a C1-2 alkylamino group. The alkyl group of the di-lower alkylamino group may be substituted with a cyano group, and examples include methyl, ethyl, cyanomethyl, cyanoethyl and the like. Preferable examples of phenyl group substituted with a di-lower alkylamino group include a 4-dimethylaminophenyl group, a 4-diethylaminophenyl group, and a 4-(cyanoethylmethylamino)phenyl group.

Examples of such the fluorescent dye are as follows:

NK-321
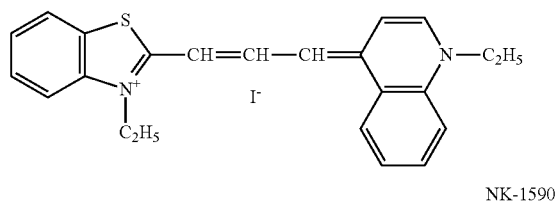

NK-1590
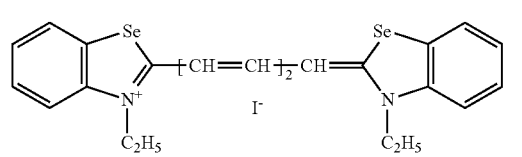

NK-529
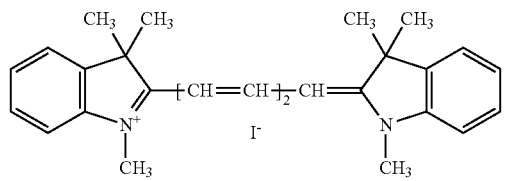

NK-2780
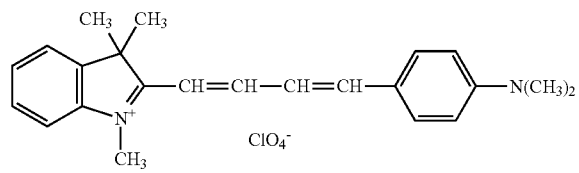

NK-1511
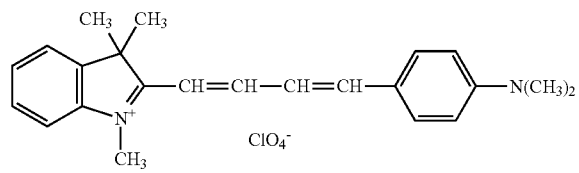

NK-376
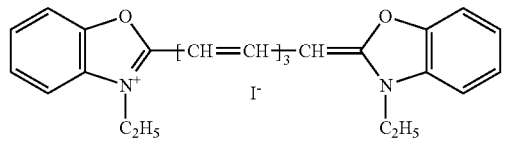

NK-2711
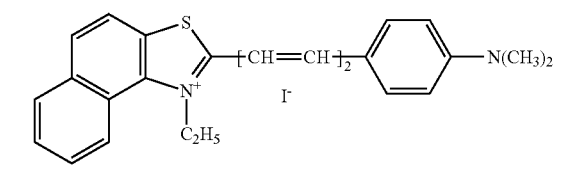

NK-136
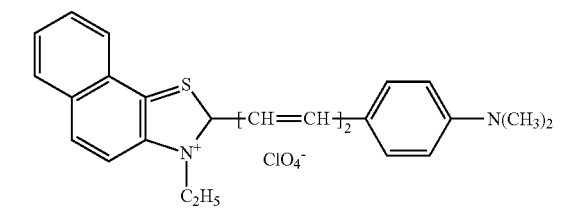

NK-2251
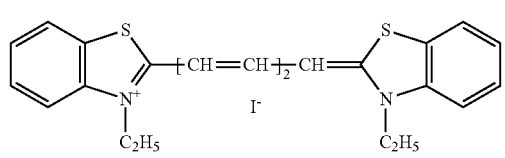

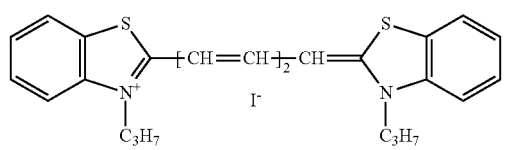

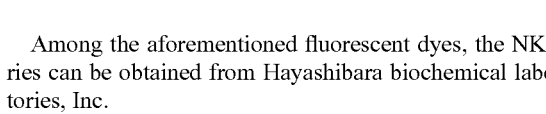

Among the aforementioned fluorescent dyes, the NK-series can be obtained from Hayashibara biochemical laboratories, Inc.

Depending on a kind of a dye and an analyzing apparatus, it is preferable that the first dye is contained in a reagent so that the final concentration in a measuring sample (mixture of reagent and urine) is 3 to 9 ppm.

(3) Second Dye

The second dye is a dye which stains sperm so that a fluorescent intensity of sperm becomes more intense than a fluorescent intensity of yeast-like fungus which underwent damage. The second dye is a dye which can stain sperm more intense than yeast-like fungus which underwent damage. And, the second dye has higher cellular membrane permeability than that of the first dye, and can fluorescently stain sperm and erythrocyte which have no damaged cellular membrane. The second dye may be a dye which is bound to or adsorbed onto a cellular membrane to stain the cellular membrane itself, or a dye which permeates through a cellular membrane to enter into a cytoplasm, to stain a substance (e.g. nucleic acid) in a cell.

It is preferable that the second dye has high permeability specific for a cellular membrane of sperm. Yeast-like fungus has various sizes and cellular membranes due to variability in its kind. Therefore, depending on a kind of fungus, damage is not given much with the fungus membrane damaging agent, and the fungus is not stained much with the first dye in some cases. In the case of such the yeast-like fungus having a small size, since a size and dyeability with the first dye are similar to those of sperm, it is difficult to distinguish yeast-like fungus and sperm. Then, by using the second dye which has higher membrane permeability than that of the first dye, and has high membrane permeability for sperm, sperm which is stained with the first dye with difficulty is stained with the second dye. As a result, it becomes easy to distinguish sperm and yeast-like fungus.

It is preferable that such the second dye is selected from the group consisting of fluorescent dyes represented by the formula (1), the formula (2) and the formula (3) of the following chemical formulas.

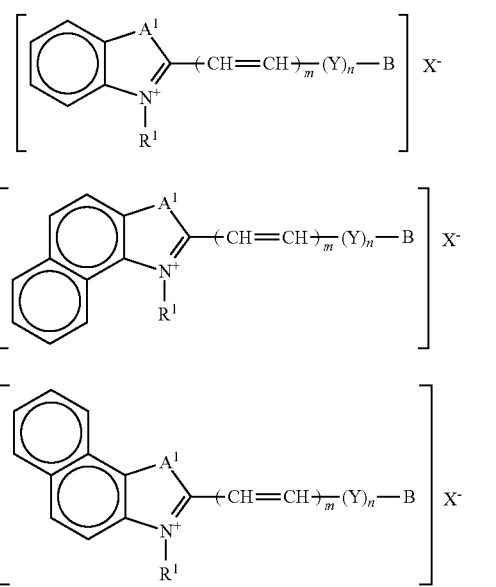

In the formula (1), the formula (2) and the formula (3), A1 is an oxygen atom, a sulfur atom, a selenium atom, or a $C(CH_3)_2$. R1 is a lower alkyl group. X is a halogen or perchloric acid. Y is a —CH= or —NH—. And, m is 1 or 2, and n is 0 or 1. B is a phenyl group substituted with two lower alkoxy groups or one di-lower alkylamino group, or a residue represented by the following formula (4) or the following formula (5). A lower alkyl group of the di-lower alkylamino group may be substituted with a cyano group.

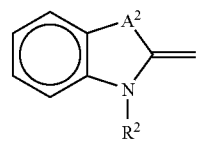

In the formula (4), A2 is an oxygen atom, a sulfur atom, or a $C(CH_3)_2$ group. R2 is a lower alkyl group.

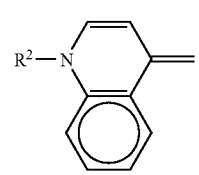

In the formula (5), R2 is a lower alkyl group.

In the formulas (1) to (5), A1 and A2 may be the same or different. And, R1 and R2 may be the same or different.

The lower alkyl group means an alkyl group of a carbon number of 1 to 6, and examples include methyl, ethyl, propyl, butyl, isobutyl, pentyl, hexyl and the like. Examples of the halogen atom of X include fluorine, chlorine, bromine and iodine. The phenyl group substituted with two lower alkoxy groups in B refers to a phenyl group substituted with two C1-3 alkoxy groups, preferably C1-2 alkoxy groups (e.g. methoxy group, ethoxy group). Specific examples include a 2,6-dimethoxyphenyl group, and a 2,6-diethoxyphenyl group. And, the phenyl group substituted with a di-lower alkylamino group in B refers to a phenyl group substituted with a C1-3 alkylamino group, preferably a C1-2 alkylamino group. The alkyl group of the di-lower alkylamino group may be substituted with a cyano group, and examples include methyl, ethyl, cyanomethyl, cyanoethyl and the like. Preferable examples of the phenyl group substituted with a di-lower alkylamino group include a 4-dimethylaminophenyl group, a 4-diethylaminophenyl group, and a 4-(cyanoethylmethylamino)phenyl group.

Examples of such the fluorescent dye are as follows:

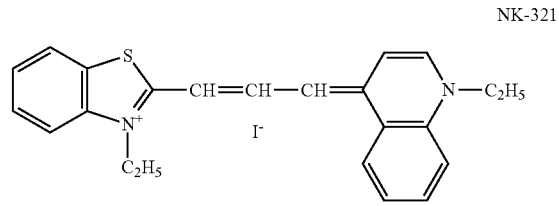

NK-321

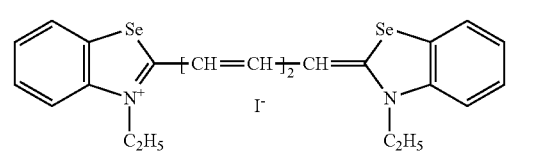

NK-1590

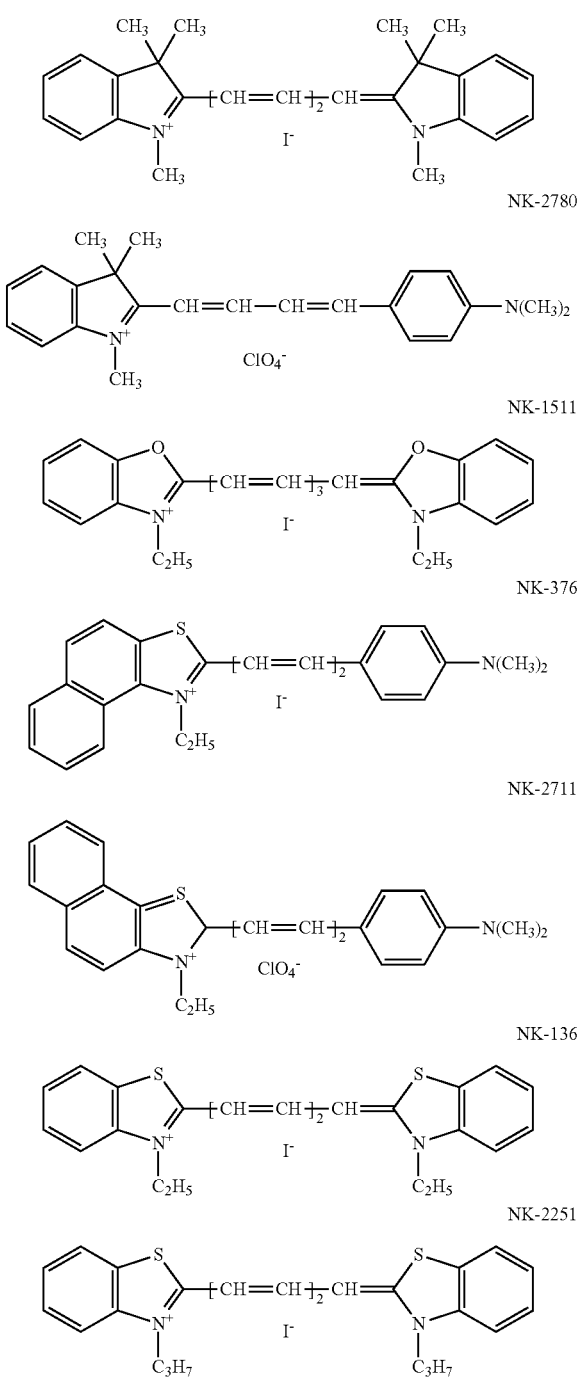

Among the aforementioned fluorescent dyes, the NK-series can be obtained from Hayashibara biochemical laboratories, Inc.

Dyes represented by the formula (1), the formula (2) and the formula (3) exemplified as the second dye are the same as dyes represented by the formula (1), the formula (2) and the formula (3) exemplified as the first dye. Therefore, when the first dye is selected from a group of dyes represented by the formula (1), the formula (2) and the formula (3), it is preferable that the second dye has higher membrane permeability than that of the first dye, particularly has higher permeability for a cellular membrane of sperm than that of the first dye.

A combination of such the first dye and second dye is, for example, a combination in which R1 or A1 is different in fluorescent dyes represented by the formula (1), the formula (2) and the formula (3). By changing a carbon number of an alkyl group of R1, membrane permeability can be changed. For example, a dye in which R1 is an ethyl group or a propyl group (e.g. NK-136 or NK-2251) has higher membrane permeability than a dye in which R1 is a methyl group (e.g. NK529). Generally, in dyes represented by the formula (1), the formula (2) and the formula (3), as a carbon number of R1 is larger, membrane permeability grows higher. Therefore, it is preferable that a carbon number of R1 of the second dye is more than a carbon number of R1 of the first dye.

The first dye and the second dye may be different or the same in a maximum absorption wavelength. When maximum absorption wavelengths of the first dye and the second dye are different, upon analysis of urine, an analyzing apparatus provided with not only a light source for exciting the first dye but also a light source for exciting the second dye can be used. On the other hand, when a light source which irradiates only the light of one kind of wavelength is used, for example, this wavelength is an absorption wavelength of the first dye, preferably also an absorption wavelength of a second dye, and preferably a maximum absorption wavelength of the first dye. In addition, when a light source having a maximum absorption wavelength of the first dye is used, the second dye may be excited with the light emitted from the first dye. It is preferable that the light emitted from at least one dye does not quench other fluorescence.

When exciting lights of the first dye and the second dye are different, it is preferable that a maximum absorption wavelength of the first dye is 630 to 640 nm, and a maximum absorption wavelength of the second dye is 640 to 660 nm.

For example, when a red laser of 633 nm is used, it is preferable that NK-529 is used as the first dye; and NK-136 and/or NK2251 is used as the second dye.

A preferable concentration of the second dye may be appropriately selected depending on a kind of a dye, an analyzing apparatus to be used and, further, a combination with a kind of the first dye.

Letting a concentration of the second dye in a measuring sample prepared by mixing urine and a reagent to be the final concentration, for example, when NK-529 is used as the first dye, and NK-136 is used as the second dye, the final concentration is preferably 0.1 to 1.2 ppm, more preferably 0.3 to 0.6 ppm.

(4) Other Components

It is preferable that the reagent for analyzing urine of the present embodiment contains the following components in addition to the fungus membrane damaging agent, the first dye and the second dye.

(4-1) Buffer

It is preferable that a buffer is contained in order to retain the buffering ability in such a pH range so that a cellular membrane of erythrocyte or sperm is not damaged.

It is preferable to use a buffer so that a pH of the reagent becomes in a range of 5.0 to 9.0, preferably 6.5 to 8.6, more preferably 7.0 to 7.8. When a pH of the reagent becomes strongly alkaline exceeding 9.0, there is a possibility that erythrocyte is hemolyzed. On the other hand, when a pH is lower than 5.0, there is a possibility that erythrocyte is damaged, and dyeability of a urine particle is totally decreased.

The buffer may be a buffer which can retain a pH of the reagent in a desired range. As the buffer, Tris and a Good buffer such as MES, Bis-Tris, ADA, PIPES, ACES, MOPSO, BES, MOPS, TES, HEPES, DIPSO, TAPSO, POPSO, HEPSO, EPPS, Tricine, Bicine and TAPS can be used. Among them, HEPES is preferably used. The buffer is used at such a concentration that a pH is in a constant range when mixed with urine, depending on the buffering ability of the buffer. Specifically, the buffer is used at 20 to 500 mM, preferably 50 to 200 mM.

(4-2) Osmotic Pressure Compensation Agent

Further, it is preferable that an osmotic pressure compensation agent is contained in order to retain an osmotic pressure at which a cellular membrane of erythrocyte or sperm is not damaged. An osmotic pressure of urine is in a wide range of 50 to 1300 mOsm/kg. When an osmotic pressure of an analysis reagent is too low, hemolysis of erythrocyte progresses early. On the other hand, when the osmotic pressure is too high, damage of a urine particle in urine becomes great. Therefore, an osmotic pressure is preferably 100 to 600 mOsm/kg, more preferably 150 to 500 mOsm/kg.

Examples of the osmotic pressure compensation agent used for retaining an osmotic pressure at such the osmotic pressure include inorganic salts, organic salts such as propionate, and sugars. As inorganic salts, sodium chloride, potassium chloride, sodium bromide and the like are used. Among organic salts, as propionate, sodium propionate, potassium propionate, ammonium propionate and the like are used. As other organic salts, oxalate, acetate and the like are used. As sugars, sorbitol, glucose, mannitol and the like are used.

(4-3) Chelating Agent

In order to reduce influence of non-crystalline salts (e.g. ammonium phosphate, magnesium phosphate, calcium carbonate) appearing in urine in analysis of urine, a chelating agent for dissolving non-crystalline salts may be contained. The chelating agent may be a de-calcium agent or de-magnesium agent, and a kind is not particularly limited. Examples include EDTA salt, CyDTA, DHEG, DPTA-OH, EDDA, EDDP, GEDTA, HDTA, HIDA, Methyl-EDTA, NTA, NTP, NTPO, EDDPO and the like. Preferably, EDTA salt, CyDTA and GEDTA are used.

Letting a concentration of the chelating agent to be contained in a measuring sample prepared by mixing with urine to be the final concentration, the chelating agent may be contained in the reagent in such a range that the final concentration becomes 0.05 to 5 W/W %, preferably 0.1 to 1 W/W %.

(4-4) Surfactant

In order to improve solubility of the fungus membrane damaging agent, the reagent may contain a surfactant such as myristyltrimethylammonium bromide (MTAB), decyltrimethylammonium bromide (DTAB), octyltrimethylammonium bromide (OTAB) and the like. When a concentration of the surfactant in a reagent is high, there is a possibility that a cellular membrane of erythrocyte or sperm is dissolved out. Therefore, it is preferable that the surfactant is contained in the reagent at such an extent of a concentration that erythrocyte is not hemolyzed, further a cellular membrane of sperm is not damaged.

(5) Reagent Kit

The reagent for analyzing urine of the present embodiment may be a reagent in which all of the fungus membrane damaging agent, the first dye and the second dye and, further, if necessary, other components such as a buffer are contained in the same container, being not limiting.

From a viewpoint of stability of the first dye and the second dye, it is preferable that a first reagent containing the fungus membrane damaging agent is contained in a first container, and a second reagent containing the first dye and the second dye is contained in a second container, and a reagent kit provided with them is prepared.

In the case of the reagent kit, it is preferable that the buffer, the osmotic pressure compensation reagent, the surfactant and the chelating agent are contained in the first reagent containing the fungus membrane damaging agent.

On the other hand, since dyes of the above-exemplified first dye and second dye are degraded in an aqueous solution in many cases, it is preferable that the second reagent is such that the first dye and the second dye are dissolved in a water-soluble organic solvent.

As the water-soluble organic solvent, lower alkanol, lower alkylene glycol, and lower alkylene glycol mono-lower alkyl ether are preferably used. For example, methanol, ethanol, n-propanol, ethylene glycol, diethylene glycol, triethylene glycol, ethylene glycol monomethyl ether, and ethylene glycol monoethyl ether can be used. Among them, glycols such as ethylene glycol, diethylene glycol, triethylene glycol and the like are preferable. In view of a viscosity and influence on a urine particle in urine, ethylene glycol is more preferably used.

Method for Analyzing Urine

The method for analyzing urine of the present embodiment comprises a step of preparing a measuring sample by fluorescent staining treatment for urine, a step of obtaining scattered light information and fluorescence information from the measuring sample by irradiating the measuring sample with light, and a step of differentiating sperm based on obtained information. By the fluorescent staining treatment, a cell membrane of yeast-like fungus is damaged without substantially damaging a cellular membrane of erythrocyte, and erythrocyte, yeast-like fungus and sperm are stained so that a fluorescent intensity of yeast-like fungus becomes more intense than a fluorescent intensity of erythrocyte, and a fluorescent intensity of sperm becomes more intense than the fluorescent intensity of yeast-like fungus. Therefore, by this method, sperm among urine particles contained in urine can be precisely differentiated. In addition, in the differentiating step, when erythrocyte and yeast-like fungus are also made to be differentiated, erythrocyte and yeast-like fungus can be precisely differentiated, respectively. Further, by adding a step of counting differentiated sperms, sperm can be precisely counted.

In the step of preparing a measuring sample, urine is fluorescent staining-treated to prepare a measuring sample. The fluorescent staining treatment gives damage to a cellular membrane for yeast-like fungus in urine, does not substantially give damage for erythrocyte in urine and, further, fluorescently stains erythrocyte, yeast-like fungus and sperm so that a fluorescent intensity of yeast-like fungus becomes more intense than a fluorescent intensity of erythrocyte, and a fluorescent intensity of sperm becomes more intense than the fluorescent intensity of yeast-like fungus. Specifically, this treatment can be performed by mixing the reagent for analyzing urine with urine.

When urine and the reagent for analyzing urine are mixed, a cellular membrane of yeast-like fungus is damaged with the fungus membrane damaging agent in the reagent. And, by passage of the first dye in the reagent through the damaged cellular membrane, yeast-like fungus is stained. On the other hand, since erythrocyte which was not hemolyzed with the fungus membrane damaging agent is less stained with the first dye than yeast-like fungus, consequently, the erythrocyte is stained so that a fluorescent intensity of yeast-like fungus becomes more intense than a fluorescent intensity of erythrocyte. In addition, since the fungus membrane damaging agent does not substantially act on sperm, a cellular membrane of sperm is not substantially damaged, but sperm is stained by binding of the first dye with a cellular membrane of sperm.

The second dye has greater membrane permeability than that of the first dye and, further, has higher specificity for a cellular membrane of sperm. Therefore the second dye binds to the cellular membrane of sperm even when the membrane is not damaged, and it becomes possible to stain the whole cellular membrane of sperm, sometimes, also the interior of a cytoplasm of sperm. As a result, fluorescent staining treatment is performed with the second dye so that a fluorescent intensity of sperm becomes more intense than a fluorescent intensity of yeast-like fungus.

Light used in the step of obtaining scattered light information and fluorescence information may excite at least one of the first dye and the second dye, and light exciting both of them is preferable. When light exciting only one of dyes is irradiated, it is necessary that the other dye is excited with fluorescence radiated from, for example, an excited dye. That is, in such the case, it is preferable that, as a combination of dyes contained in a reagent for analyzing urine used, dyes in a combination in which both dyes are excited are contained.

When a measuring sample prepared using the reagent for analyzing urine is irradiated with light, the first dye and the second dye in the measuring sample are excited. Thereby, scattered light information showing information on a form of a urine particle in the measuring sample, and fluorescence information showing information on a staining intensity of a urine particle can be obtaining.

It is preferable that scattered light information and fluorescence information from the measuring sample are obtained by introducing the measuring sample into a flowcell of a flowcytometer, and irradiating the measuring sample flowing in the flowcell with excitation light exciting a fluorescent dye.

The scattered light information is preferably a scattered light intensity, more preferably a forward scattered light intensity. The forward scattered light intensity generally reflects information corresponding to a size of a cell.

The fluorescence information is preferably a fluorescent intensity. The fluorescent intensity reflects an intensity of fluorescent staining of a cell.

In the differentiation step, sperm and other urine particle in urine are differentiated based on the obtained scattered light information and fluorescent information. As described above, in the step of preparing the measuring sample, erythrocyte, yeast-like fungus and sperm are fluorescently stained so that a fluorescent intensity of yeast-like fungus becomes more intense than a fluorescent intensity of erythrocyte, and a fluorescent intensity of sperm becomes more intense than the fluorescent intensity of yeast-like fungus. Therefore, by using the scattered light information and the fluorescence information, sperm in urine can be precisely differentiated. For example, in the differentiation step, by producing a scattering diagram using a scattered light intensity and a fluorescent intensity as two axes, and specifying a region where sperm appears, sperm can be differentiated. In addition, in the differentiation step, based on the scattered light information and the fluorescence information, erythrocyte and yeast-like fungus can be also precisely differentiated. For example, by producing a scattering diagram using a scattered light intensity and a fluorescent intensity as axes, and specifying regions where erythrocyte and yeast-like fungus appear, respectively, erythrocyte and yeast-like fungus can be differentiated, respectively.

Further, by adding a step of counting differentiated sperm, sperm can be precisely counted. In addition, if erythrocyte and yeast-like fungus are also differentiated in the differentiation step, erythrocyte and yeast-like fungus can be also precisely counted in the counting step.

Figure 2:
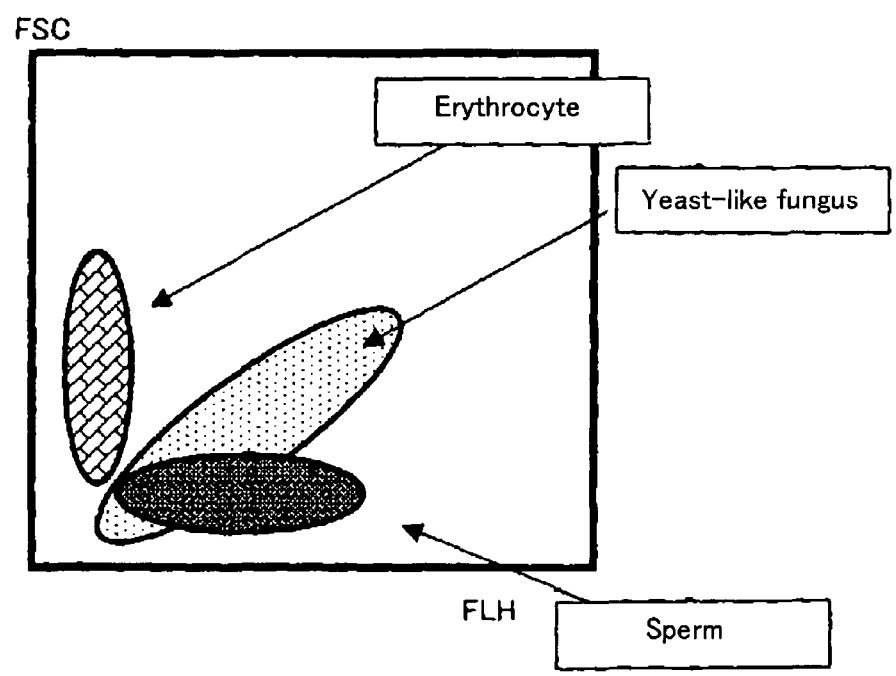
FIG. 2 is a conceptional view of a scattering diagram obtained when urine containing sperm and yeast-like fungus is measured using a reagent containing a first dye.

FIG. 1 is a conceptional view of a scattering diagram obtained when urine is analyzed by the aforementioned method using the reagent for analyzing urine (i.e. reagent for analyzing urine containing the fungus membrane damaging agent, the first dye and the second dye). For reference, a conceptional view of a scattering diagram obtained when urine is analyzed by the aforementioned method using a reagent containing the fungus membrane damaging agent and the first agent but not containing the second dye is shown in FIG. 2. In both cases, an ordinate axes is a scattered light intensity, and an abscissa axis is a fluorescent intensity. When the reagent for analyzing urine containing the fungus membrane damaging agent, the first dye and the second dye is used, yeast-like fungus is stained also with the first dye. As a result, as shown in FIG. 1, in a scattering diagram, a population of yeast-like fungus appears at a position having a higher fluorescent intensity relative to a region where a population of erythrocyte appears (hereinafter, referred to as erythrocyte region). Also in the case where a reagent containing the fungus membrane damaging agent and the first dye but not containing the second dye is used, as shown in FIG. 2, in a scattering diagram, a population of yeast-like fungus appears at a position having a higher fluorescent intensity relative to an erythrocyte region. However, since this reagent does not contain the second dye, in FIG. 2, a region where a population of sperm appears (hereinafter referred to as sperm region) is overlapped with a part of a region where a population of yeast-like fungus appears (hereinafter, referred to as yeast-like fungus region). To the contrary, when a reagent for analyzing urine containing the fungus membrane damaging agent, the first dye and the second dye is used, sperm is stained with the first dye and, further, stained with the second dye. As a result, as shown in FIG. 1, since a sperm region is sifted towards a higher fluorescent intensity, it becomes possible to avoid overlapping with a yeast-like fungus region. Thereby, it becomes possible to precisely differentiate a yeast-like fungus population and a sperm population.

In addition, when a reagent for analyzing urine containing the fungus membrane damaging agent, the first dye and the second dye is used, as shown in FIG. 1, since an erythrocyte region, a yeast-like fungus population, and a sperm population are clearly differentiated, respectively, the number and a content of each urine particle in a sample can be obtained by counting each population.

Flowcytometer

Examples of an apparatus for analyzing urine to which the reagent for analyzing urine of the present embodiment is applied include an apparatus for analyzing urine provided with:

a excitation light source for irradiating light having an excitation wavelength of the fluorescent dye;

an optical receiver for receiving scattered light and fluorescence emitted from a urine particle in a sample;

an information treating means for treating information on received scattered light and information on received fluorescence, and determining whether the urine particle is any of erythrocyte, yeast-like fungus, and sperm.

It is preferable that the information on scattered light is a scattered light intensity, and the information on fluorescence is a fluorescent intensity.

It is preferable that the information treating means is provided with a counting means for differentiating and counting erythrocyte, yeast-like fungus and sperm contained in the urine by determining whether the obtained scattered light intensity and fluorescent intensity correspond to any of erythrocyte, yeast-like fungus, and sperm.

It is preferable that the counting means produces a scattering diagram using a forward scattered light intensity and a fluorescent intensity as two axes, specifies an erythrocyte population, a yeast-like fungus population, and a sperm population, and counts the dot number contained in the populations. Alternatively, the information treating means may be provided with an operation means for calculating an average fluorescent intensity and an average scattered light intensity in a specified population.

Specification of a sperm population may be performed based on, for example, comparison between a scattering diagram obtained from scattered light information and fluorescent information of a comparative sample obtained by mixing a reagent not containing a second dye with a urine specimen, and a scattering diagram obtained from scattered light information and fluorescent information of a measuring sample obtained by mixing the reagent of the present invention and a urine specimen.

The analyzing apparatus may be further provided with a display part for displaying the produced scattering diagrams and operation result.

EXAMPLES

Method for Preparing Measuring Sample (1) First Reagent 2-phenoxyethanol was used as a fungus membrane damaging agent. A first reagent containing 2-phenoxyethanol, a buffer, an osmotic pressure compensation agent, a chelating agent and a pH adjusting agent at concentrations shown below was prepared

| | |
|---|---|
| HEPES | 11.9 g/l |
| Sodium propionate | 5.98 g/l |
| EDTA-3K | 4.0 g/l |
| 2-Phenoxyethanol | 7.5 g/l |
| Sodium hydroxide | Amount so as to bring pH into 7.2 |

(2) Second reagent
(2-1) Second Reagent A:

NK529 as a first dye was dissolved in diethylene glycol to prepare a second reagent A.

NK529 is excited with red laser light (wavelength 635 nm) emitted from an excitation light source mounted in a flowcytometer used in the present Example. The flowcytometer used in the present Example is Automated Urine Cell Analyzer UF110i (manufactured by Sysmex) in which an argon laser light source (488 nm) is replaced with a semiconductor laser light source (635 nm). Hereinafter, this is simply referred to as flowcytometer.
(2-2) Second Reagent B NK529 as the first dye and NK136 as the second dye were dissolved in diethylene glycol to prepare a second reagent B.
(2-3) Second Reagent C NK529 as the first dye and NK2251 as the second dye were dissolved in diethylene glycol to prepare a second reagent C.
(3) Mixing with Urine Specimen A urine specimen and the first reagent were mixed at a ratio of 1:3 and, further, the second reagent was mixed so that the final concentration of the first dye became 6 ppm, to obtain a measuring sample.

(Relationship Between Concentration of Second Dye and Dyeability of Sperm)

Using six kinds of second reagents B having a different concentration of the second dye, relationship between a concentration of the second dye and dyeability of sperm was investigated. NK529 as the first dye was contained in a second reagent B at such an amount that the final concentration in the measuring sample became 6 ppm. NK136 as the second dye was contained in a second reagent B so that the final concentration became 0.3 ppm, 0.6 ppm, 1.2 ppm, 1.5 ppm, 3 ppm or 6 ppm.

Using the second reagents B, the first reagent and a urine specimen in which sperm appears, six kinds of measuring samples were prepared. Each measuring sample was introduced into a flowcytometer, and a fluorescent intensity was measured.

In addition, the second reagent A was used in place of the second reagent B to prepare a measuring sample according to the same manner, this was introduced into a flowcytometer, and a fluorescent intensity at a content of NK136 of 0 ppm was measured.

Figure 3:
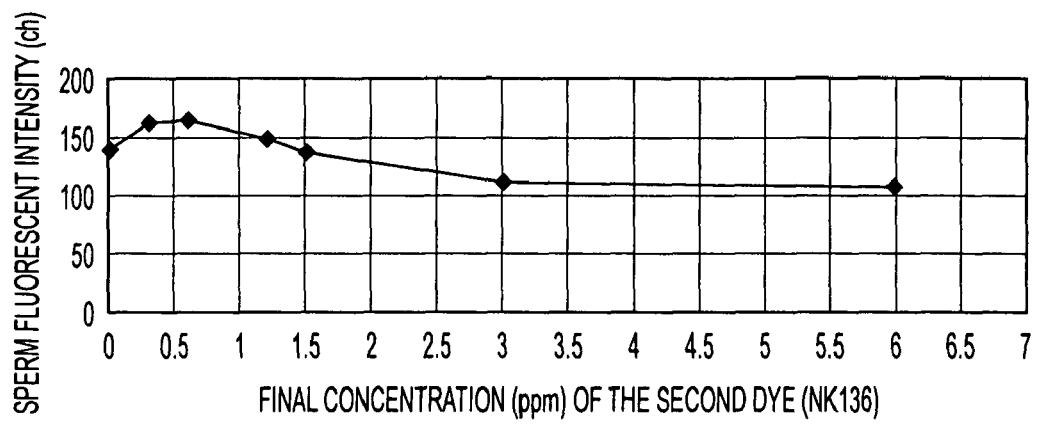
FIG. 3 is a graph showing a relationship between a concentration of NK136 and dyeability of sperm.

These results are shown in FIG. 3. In FIG. 3, an ordinate axis is a fluorescent intensity, and an abscissa axis is a concentration (final concentration) of NK136 which is the second dye.

From FIG. 3, it was found that a fluorescent intensity is increased when a concentration of NK136 is within range of 0.3 to 1.2 ppm. It was found that a fluorescent intensity is not increased when a concentration of NK136 is 1.5 ppm or more.
(Analysis of Urine Specimen 1)

As a urine specimen 1, human urine in which sperm appears was used.

Example 1

As a second reagent, the second reagent B prepared so that the final concentration of NK529 became 6 ppm, and the final concentration of NK136 became 0.6 ppm, was used.

The urine specimen 1 was mixed with the first reagent and, further, the mixture was mixed with the second reagent B to prepare a measuring sample from the urine specimen 1.

Figure 4:
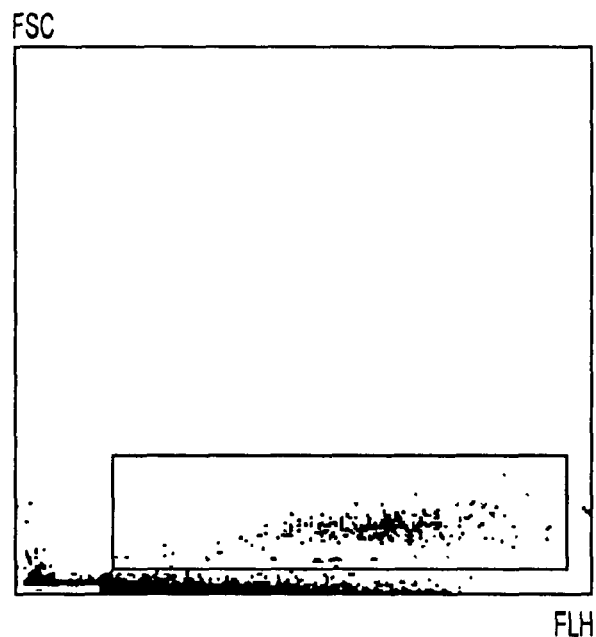
FIG. 4 is a scattering diagram obtained in Example 1.

The prepared measuring sample was introduced into a flowcell, and a light intensity was measured with a flowcytometer to produce a two-dimensional scattering diagram using a fluorescent intensity (abscissa axis) and a forward scattered light intensity (ordinate axis) as two axes. The resulting scattering diagram is shown in FIG. 4. In addition, in the scattering diagram, a region thought that sperm appears (region surrounded with a solid line in a scattering diagram) was specified. An average of a fluorescent intensity detected from sperm appearing in the region was 165.

Comparative Example 1

According to the same manner as that of Example 1 except that the second reagent A (final concentration of NK529 was 6 ppm) was used, a measuring sample was prepared from a urine specimen 1.

Figure 5:
FIG. 5 is a scattering diagram obtained in Comparative Example 1.

The prepared measuring sample was introduced into a flowcell, a light intensity was measured with a flowcytometer, and a two-dimensional scattering diagram using a fluorescent intensity (abscissa axis) and a forward scattered light intensity (ordinate axis) as two axes was produced. The resulting scattering diagram is shown in FIG. 5. In the scattering diagram, a region thought that sperm appears (region surrounded with a solid line in a scattering diagram) was specified. An average of a fluorescent intensity detected from sperm appearing in the region was 110.

From comparison between FIG. 4 and FIG. 5, and the resulting each average fluorescent intensity, it is found that, a sperm population appears in a region having a high fluorescent intensity when a reagent containing NK136 as the second dye (Example 1) is used.

(Analysis of Urine Specimen 2)

As a urine specimen 2, human urine in which yeast-like fungus appears was used.

Example 2

As a second reagent, the second reagent B prepared so that the final concentration of NK529 became 6 ppm, and the final concentration of NK136 became 0.6 ppm, was used.

The urine specimen 2 was mixed with the first reagent and, further, the mixture was mixed with the second reagent B to prepare a measuring sample from a urine specimen 2.

Figure 6:
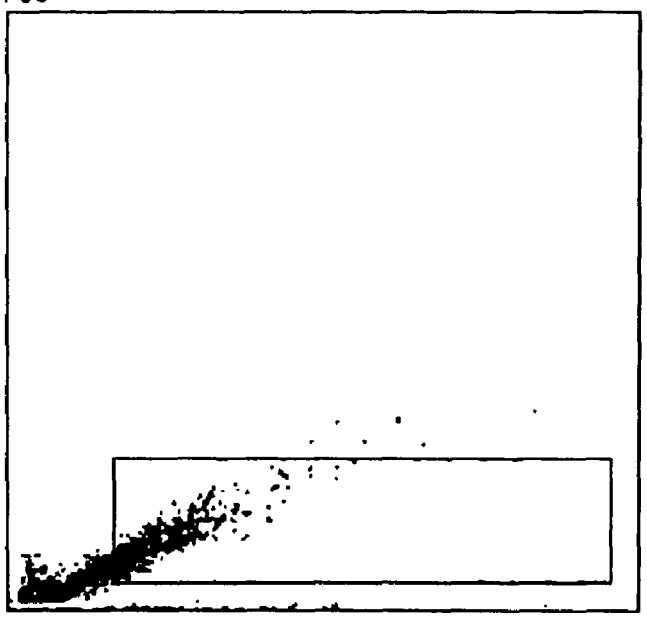
FIG. 6 is a scattering diagram obtained in Example 2.

The prepared measuring sample was introduced into a flowcell, a light intensity was measured with a flowcytometer, and a two-dimensional scattering diagram using a fluorescent intensity (abscissa axis) and a forward scattered light intensity (ordinate axis) as two axes was produced. The resulting scattering diagram is shown in FIG. 6. In addition, in the scattering diagram, an average fluorescent intensity of a region thought that sperm appears (in the figure, a part surrounded with a solid line) was calculated, and found to be 87.

Comparative Example 2

According to the same manner as that of Example 2 except that the second reagent A (dye final concentration of NK529 was 6 ppm), a measuring sample was prepared from a urine specimen 2.

Figure 7:
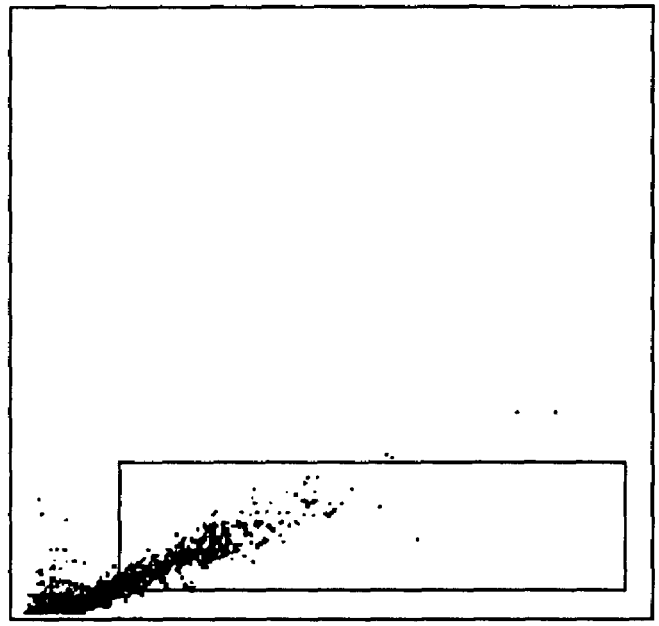
FIG. 7 is a scattering diagram obtained in Comparative Example 2.

The prepared measuring sample was introduced into a flowcell, a light intensity was measured with a flowcytometer, and a two-dimensional scattering diagram using a fluorescent intensity (abscissa axis) and a forward scattered light intensity (ordinate axis) as two axes was produced. The resulting scattering diagram is shown in FIG. 7. In addition, in the scattering diagram, a region thought that sperm appears (region surrounded with a solid line in a scattering diagram) was specified. An average of a fluorescent intensity detected from sperm appearing in this region was 87.

From comparison between FIG. 6 and FIG. 7, and the resulting each average fluorescent intensity, it is found that the second dye in the reagent does not substantially influence on a position of appearance of yeast-like fungus.

(Analysis of Urine Specimen 3)

As a urine specimen 3, human urine in which sperm appears was used.

Example 3

As a second reagent, the second reagent C prepared so that the final concentration of NK529 became 6 ppm, and the final concentration of NK2251 became 0.6 ppm, was used.

The urine specimen 3 was mixed with the first reagent and, further, the mixture was mixed with the second reagent C to prepare a measuring sample from the urine specimen 3.

Figure 8:
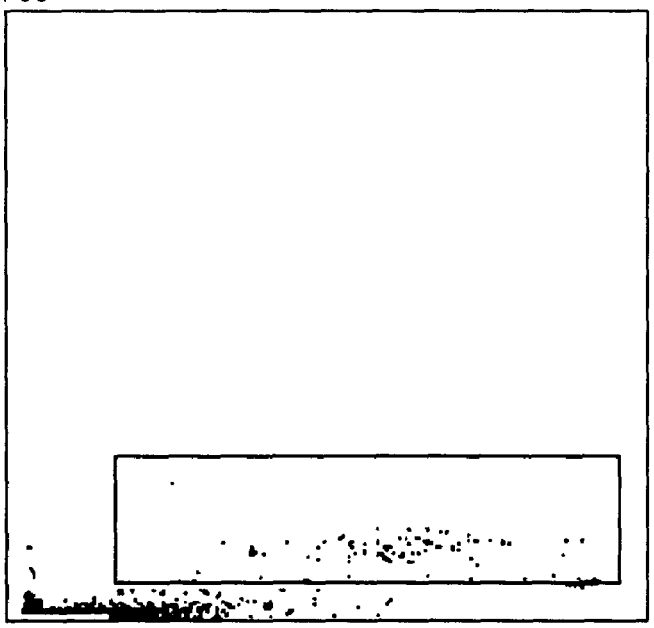
FIG. 8 is a scattering diagram obtained in Example 3.

The prepared measuring sample was introduced into a flowcell, a light intensity was measured with a flowcytometer, and a two-dimensional scattering diagram using a fluorescent intensity (abscissa axis) and a forward scattered light (ordinate axis) as two axes was produced. The resulting scattering diagram is shown in FIG. 8. In addition, in the scattering diagram, a region thought that sperm appears (region surrounded with a solid line in a scattering diagram) was specified. An average of a fluorescent intensity detected from sperm appearing in this region was 165.

Comparative Example 3

Figure 9:
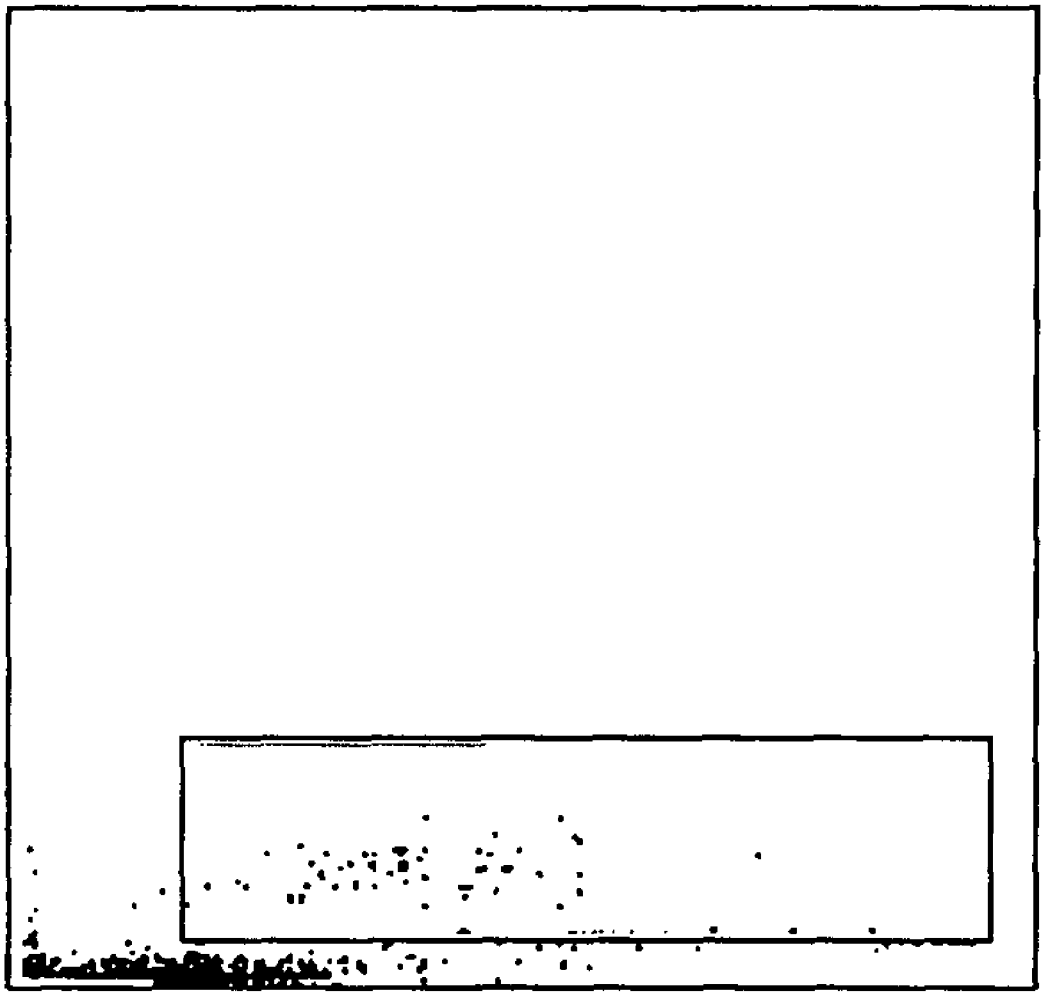
FIG. 9 is a scattering diagram obtained in Comparative Example 3.

Using the second reagent A (dye final concentration of NK529 was 6 ppm), according to the same manner as that of Example 3, a measuring sample was prepared from a urine specimen 3, a light intensity was measured with a flowcytometer, and a two-dimensional scattering diagram using a fluorescent intensity (abscissa axis) and a forward scattered light (ordinate axis) as two axes was produced. The resulting scattering diagram is shown in FIG. 9. In addition, in the scattering diagram, a region thought that sperm appears (region surrounded with a solid line in a scattering diagram) was specified. An average of a fluorescent intensity detected from sperm appearing in this region was 126.

From comparison between FIG. 8 and FIG. 9, and the resulting each average fluorescent intensity, it is found that, by using a reagent containing NK2251 as a second dye, dyeability of sperm is increased, and a position in which a sperm population appears is sifted to a right side (higher fluorescent intensity).

From the foregoing, by using a reagent for analyzing urine containing a second dye having higher membrane permeability than that of a first dye, a region thought that sperm appears is set on a higher fluorescent intensity side, thereby, it becomes possible to distinguish from a region thought that yeast-like fungus appears. Alternatively, by overlapping scattering diagrams obtained from a reagent not containing a second dye and a reagent containing a second dye, respectively, a population appearing as a difference in a higher fluorescent intensity region can be also specified as a sperm population. Therefore, by using the analysis reagent of the present invention, high precision analysis which can precisely differentiate yeast-like fungus, erythrocyte, and sperm, respectively, becomes possible.

What is claimed is:
1. A method for analyzing urine, comprising the steps of:
preparing a measuring sample by fluorescent staining treatment for urine,
wherein the fluorescent staining treatment damages a cellular membrane of yeast-like fungus in urine without substantially damaging a cellular membrane of erythrocyte in urine, and stains erythrocyte, yeast-like fungus and sperm in urine so that a fluorescent intensity of yeast-like fungus becomes more intense than that of erythrocyte, and a fluorescent intensity of sperm becomes more intense than that of yeast-like fungus;
obtaining scattered light information and fluorescence information from the measuring sample by irradiating the measuring sample with light; and
differentiating sperm contained in the measuring sample based on the scattered light information and the fluorescence information, wherein the fluorescent staining treatment is performed using
a fungus membrane damaging agent for damaging a cellular membrane of yeast-like fungus,
a first dye for staining yeast-like fungus so that a fluorescent intensity of damaged yeast-like fungus becomes more intense than that of the erythrocyte, and a second dye for staining sperm so that a fluorescent intensity of sperm becomes more intense than that of the damaged yeast-like fungus, wherein the first dye and the second dye are selected from the group consisting of fluorescent dyes represented by the following formula (1), formula (2), and formula (3):

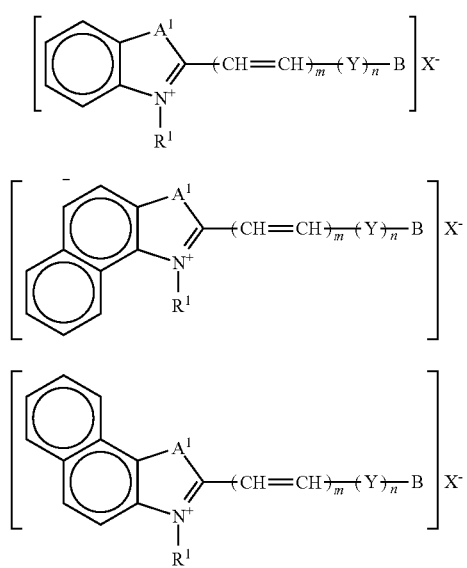

wherein $A^1$ is an oxygen atom, a sulfur atom, a selenium atom, or a $C(CH_3)_2$; $R^1$ is a lower alkyl group; X is a halogen or perchloric acid; Y is a —CH= or —NH—; m is 1 or 2; n or 0 or 1: B is (a) a phenyl group substitute with two lower alkoxy groups, a lower alkylamino group, a di-cyanoamino group or a lower alkylcyanoamino group, or (b) a residue represented by the following formula (4) or formula (5):

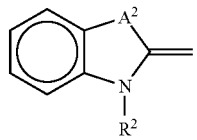

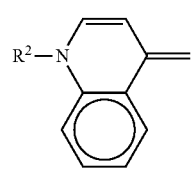

wherein $A^2$ is an oxygen atom, a sulfur atom, or a —$C(CH_3)_2$—; $R^2$ is a lower alkyl group, wherein a carbon number of $R^1$ of the second dye is more than a carbon number of $R^1$ of the first dye.

2. The method according to claim 1, wherein the fungus membrane damaging agent is selected form the group consisting of aromatic alcohol, phenyl acetate and a benzothiazole compound.

3. The method according to claim 1, wherein the second dye has higher cellular membrane permeability than that of the first dye.

4. The method according to claim 1, further comprising a step of counting differentiated sperm.

5. The method according to claim 1, wherein the scattered light information is a forward scattered light intensity, and the fluorescence information is a fluorescent intensity.

6. The method according to claim 1, wherein in the differentiation step, erythrocyte, yeast-like fungus and sperm contained in the measuring sample are differentiated, respectively.

* * * * *